United States Patent [19]
Kamiya et al.

[11] Patent Number: 5,283,053
[45] Date of Patent: Feb. 1, 1994

[54] APPARATUS FOR TREATING CONTACT LENSES AND CONTACT LENS TREATING VESSEL FOR USE THEREIN

[75] Inventors: Hideaki Kamiya, Gifu; Makoto Nakagawa, Aichi; Masashi Endo, Gifu; Masakatsu Yamauchi, Kani, all of Japan

[73] Assignee: Tomei Sangyo Kabushiki Kaisha, Nagoya, Japan

[21] Appl. No.: 963,981

[22] Filed: Oct. 21, 1992

[30] Foreign Application Priority Data

Oct. 25, 1991 [JP] Japan .................. 3-279838

[51] Int. Cl.⁵ .............. A61L 2/00; H05B 6/36; H05B 6/02
[52] U.S. Cl. .................. 422/300; 422/22; 422/27; 134/57 R; 134/105; 134/15; 219/628; 219/635; 219/647; 219/672
[58] Field of Search .............. 422/300, 22, 27; 134/57 R, 105, 158, 901; 206/5, 6, 7; 219/10.491, 10.57, 10.67, 10.75, 10.79

[56] References Cited

U.S. PATENT DOCUMENTS

| | | | |
|---|---|---|---|
| 4,600,821 | 7/1986 | Fichtner et al. | 219/10.51 |
| 4,697,605 | 10/1987 | Yung | 134/107 |
| 4,779,633 | 10/1988 | Thomas et al. | 134/93 |
| 4,784,167 | 11/1988 | Thomas et al. | 134/93 |
| 4,852,591 | 8/1989 | Wisotzki et al. | 134/57 R |
| 5,101,086 | 3/1992 | Dion | 219/10.491 |
| 5,105,841 | 4/1992 | Oguma et al. | 134/57 R |
| 5,117,849 | 6/1992 | Zimmerli | 134/57 R |
| 5,129,410 | 7/1992 | Ifejika | 134/32 |

OTHER PUBLICATIONS

Patent Abstracts of Japan, unexamined applications, section C, vol. 15, No. 289, Jul. 23, 1991, 3-103261.

Primary Examiner—James C. Housel
Assistant Examiner—N. Bhat
Attorney, Agent, or Firm—Armstrong, Westerman, Hattori, McLeland & Naughton

[57] ABSTRACT

A contact lens treating vessel equipped with an electromagnetic induction coil and a rectifier for converting an alternating current into a direct current, and an apparatus for treating contact lenses comprising a treating apparatus body for supplying electric power and the vessel which can be attached to or detached from the apparatus body, wherein the apparatus body is equipped with a magnet-generating coil and the vessel is equipped with an electromagnetic induction coil.

16 Claims, 2 Drawing Sheets

APPARATUS FOR TREATING CONTACT LENSES AND CONTACT LENS TREATING VESSEL FOR USE THEREIN

BACKGROUND OF THE INVENTION

1. Field of the Invention

The present invention relates to an apparatus for treating contact lenses and a contact lens treating vessel for use therein and, more particularly, to an apparatus for treating contact lenses, in which the contact lenses can be cleaned and sterilized by immersing the contact lenses in a treating solution for contact lenses and applying a direct current to the treating solution, and a contact lens treating vessel for use therein.

2. Description of the Related Art

In order to disinfect a contact lens, there has been proposed an apparatus for disinfecting a contact lens by applying an electric current to an electrolyte solution through electrodes where the contact lens is immersed in the electrolyte solution to carry out the electrolysis of the electrolyte solution (Japanese Unexamined Patent Publication No. 68454/1981, Japanese Unexamined Patent Publication No. 130713/1981, Japanese Unexamined Utility Model Publication No. 189021/1985 and Japanese Unexamined Utility Model Publication No. 35023/1988).

A contact lens treating vessel which is used in the above-mentioned apparatus is constructed so that the treating vessel can be attached to or detached from an apparatus body and the treating vessel in which the contact lens is stored can be a portable vessel.

However, the vessel suffers from the following defects. Dust and the like may be deposited over the electrodes of the treating vessel and the apparatus body, causing insufficient electrical contact. When the attachment and detachment of the treating vessel and the apparatus body may be repeated many times, the electrodes are worn away and insufficient electric conduction is sometimes caused. A leak of electricity is sometimes caused when the electrolyte solution the electrode of an apparatus body. Therefore, the improvement of the vessel has been needed.

An object of the present invention is to provide an apparatus for treating contact lenses, in without suffering from a sufficient electric conduction, a leak of electricity and the like due to insufficient electrical contact between electrodes.

A further object of the present invention is to provide a contact lens treating vessel for use therein.

These and other objects of the present invention will become apparent from the description hereinafter.

SUMMARY OF THE INVENTION

In accordance with the present invention, there are provided (A) an apparatus for treating contact lenses comprising a treating apparatus body for supplying electric power and a contact lens treating vessel which can be attached to or detached from the treating apparatus body, wherein the treating apparatus body is equipped with a magnetic field generating coil and the contact lens treating vessel is equipped with an electromagnetic induction coil, and a rectifier for converting an alternating current into a direct current.

DETAILED DESCRIPTION OF THE PREFERRED EMBODIMENT

The apparatus for treating contact lenses and a contact lens treating vessel for use therein, of the present invention are explained in accordance with the following drawings.

Figure 1:
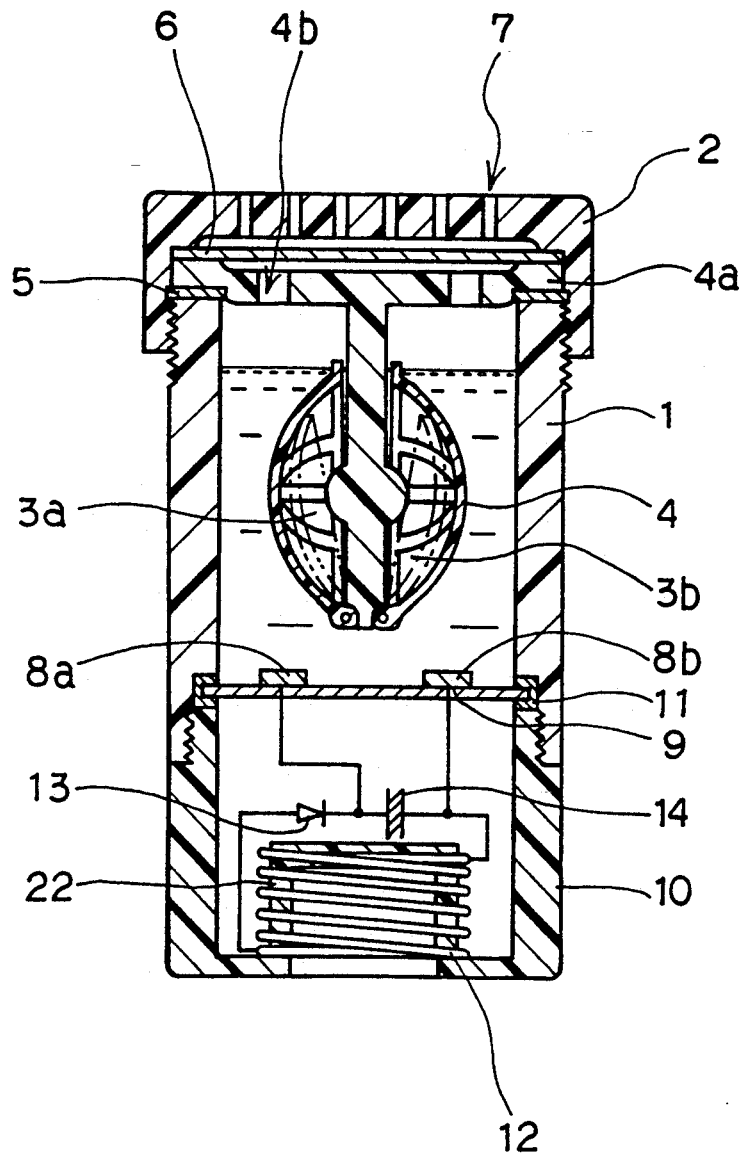
FIG. 1 shows a contact lens treating vessel of the present invention.

FIG. 1 is a cross-sectional view of the principal part of an embodiment of the contact lens treating vessel of the present invention.

Referring to FIG. 1, the numeral 1 denotes a treating vessel body. A support 4a of a basket 4 for accommodating and holding contact lenses 3a and 3b is provided between the treating vessel body 1 and a lid 2 which can be attached to or detached from the treating vessel body 1. The support 4a has some air vents 4b. As a material of the basket 4, for instance, a heat resistant resin such as polysulfone or polycarbonate, or the like, can be used.

A seal packing 5 is provided between the treating vessel body 1 and the support 4a, and a gas-permeable film 6 is provided between the support 4a and the lid 2. The gas-permeable film 6 has numerous fine pores through which vapor and gas can pass but liquid cannot pass. The lid 2 has plural air vents 7.

A pair of electrodes 8a and 8b is provided on a bottom panel 9 of the treating vessel body 1. any materials usually employed can be used for electrodes 8a and 8b without limitation. Examples include such, metals as stainless steel, platinum, gold, copper and nickel; carbon rod; a synthetic resin on which a metal such as gold or platinum is coated by plating; an insulating material, the surface of which is coated with a paste containing a metal such as gold or platinum as a main component by a printing method and then baked; an insulating material over which the metal is vapor-deposited, and the like. Among them, in consideration of dissolution of the electrodes due to electrolysis occurring on each electrode, and the like, it be desired that the electrode is made of a metal such as gold or platinum, which has a small ionization tendency and is not easily dissolved in the electrolyte solution.

The gas-permeable film 6 usually has many fine pores preferably having a diameter of 0.1 to 3.0 μm and a thickness of 75 to 700 μm or so. When the diameter of the pore is adjusted to 0.2 μm or less, contamination of the electrolyte solution can be prevented after disinfecting because microorganisms and the like are blocked by the gas-permeable film 6. Specific examples of the gas-permeable film 6, including for instance, a fluorocarbon resin film on which a polypropylene net is laminated, a hydrophobic microbial filter, a hydrophobic microfiltration membrane made of polyethylene, polypropylene or the like, silicone film, and the like. A netlike reinforcement or the like can be attached to the gas-permeable film 6.

The bottom panel 9 is provided between the treating vessel body 1 and the bottom body 10 through a seal packing 11.

The electromagnetic induction coil 12 is provided under the treating vessel body 1. The electromagnetic induction coil 12 is connected with the electrodes 8a and 8b through a lead, and a rectifier 13 and a condenser 14 are provided between the electromagnetic induction coil 12 and the electrodes 8a and 8b.

The electromagnetic induction coil 12 is used for generating an electric current by electromagnetic induction produced by a magnetic field which is generated from a magnet-generating coil. The number of turns of the electromagnetic induction coil 12 cannot be absolutely determined since the number of turns depends upon a magnetic force generated from the magnetic field generating coil. It is desired that the number of turns is adjusted so that an electric power generated from the electromagnetic induction coil 12 is generally 5 to 50 W, preferably 10 to 25 W. When the electric power is less than the above-mentioned range, there is a tendency for the electrolyte solution that is, the treating solution for the contact lenses, to be not efficiently heated. When the electric power is more than the above-mentioned range, there is a tendency for an overload current to flow in the electrolyte solution and causing damage to the electrode.

It is desirable that an electric current applied to the electrolyte solution is 0.01 to 5 A, preferably 0.05 to 0.5 A so that stains such as proteins which tend to adhere to a lens during usual wearing can be removed. When the electric current is less than the above-mentioned range, peroxides are not sufficiently generated in the electrolyte solution during the application of an electric current to the solution, thereby failing to provide removal of proteins. Also, when the electric current exceeds the above-mentioned range, the reaction becomes radical on the electrodes, thereby damaging the electrodes while sufficiently removing proteins.

The rectifier 13 is used for obtaining secondary power by rectifying secondary voltage which is generated during the application of an electric current of a primary circuit.

Specific examples of the rectifier 13, includes, for instance, a silicone diode and the like. Since the silicone diode has a relatively high operating frequency, rectifiers having a short reverse recovery time such as a fast recovery diode and a shottky barrier diode, are preferable from the viewpoint of efficiency.

A capacitor 14 is used for producing smoothed voltage by accumulating half-wave DC voltage which is obtained by the rectifier 13. The capacitor 14 can impart approximately constant voltage to the electrodes 8a and 8b.

Capacity of the capacitor 14 depends upon the oscillation frequency of a magnetic circuit. It is desired that the capacity is 0.1 to 100 $\mu F$ or so, preferably 0.1 to 10 $\mu F$ or so in consideration of the outside dimension of the capacitor for accommodating the capacitor within in the contact lens treating vessel.

According to the present invention, treatment of the contact lens can be carried out without the capacitor 14. When the capacitor 14 is not used, voltage which is applied to the electrodes is varied, greatly therefore, the peak voltage and peak current at the electrodes become higher and good results in safety for electric shock, for reducing the reliability of the electrode. Therefore, the use of the capacitor is preferred.

Figure 2:
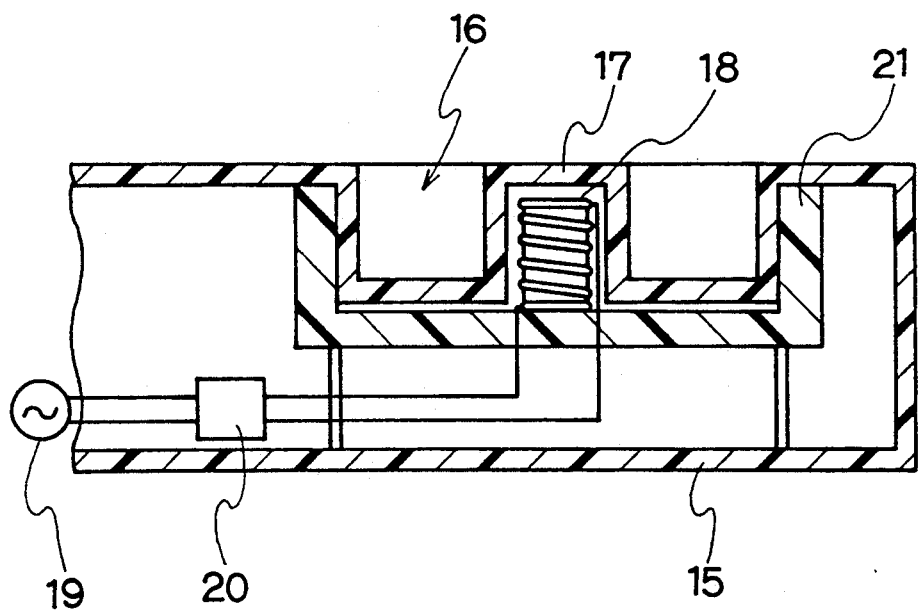
FIG. 2 shows a treating apparatus body used in an apparatus for treating contact lenses of the present invention.

FIG. 2 is a cross-sectional view of the principal part of an embodiment of the treating apparatus body used in the apparatus for treating contact lenses of the present invention.

Referring to FIG. 2, the numeral 15 denotes a treating apparatus body. The treating apparatus body 15 is equipped with a bezel for attachment and detachment 16, which is used for installing the contact lens treating vessel, and a projection for electromagnetic induction 17.

The projection for electromagnetic induction 17 is inserted into the inside of the electromagnetic induction coil 12. A magnetic field generating coil 18 is provided inside the projection for electromagnetic induction 17.

The magnetic field generating coil 18 is used for generating electromagnetism and transmitting the electromagnetism to the electromagnetic induction coil 12. The number of turns of the magnetic field generating coil 18 cannot be absolutely determined since the number of turns depends upon oscillation frequency, output, the shape of a core, voltage of power source and the like. The number of turns is preferably, 200 turns.

Electricity is supplied from a general domestic electric source having a frequency of 50 to 60 Hz and an AC voltage of 100 V through a plug 19 to the magnet-generating coil 18. After the AC voltage is converted into DC voltage, which is a power for a high-frequency oscillation circuit, a high-frequency current flows from the high-frequency oscillation circuit 20. The higher the frequency of the high-frequency current is, the more miniaturized the apparatus for treating contact lenses may be. Conversely, miniaturization causes the price of a circuit element to become higher and affection of noise due to the high frequency to a radio and a TV set becomes greater. Generally, it is desired that the frequency of the high-frequency current is 100 Hz to 1 MHz, preferably 1 KHz to 100 KHz.

In order to improve magnetic induction efficiency, it is desired that a ferrite core is provided inside the magnetic field generating coil 18. In FIG. 2, an E-type ferrite core 21 is used. The E-type ferrite core 21 is also used as a ferrite core of the electromagnetic induction coil 12.

The apparatus for treating contact lenses of the present invention has an electromagnetic induction coil and a magnetic field generating coil in the contact lens treating vessel and the treating apparatus body, respectively. Therefore, when the apparatus is made of, for instance, a synthetic resin or the like so that water and the like could not invade the apparatus, a liquidtight state could be maintained while electrically insulating the inside of the apparatus from outside thereof, thus reducing the possibility of leaking electricity. Furthermore, since the contact lens treating vessel is connected with the treating apparatus body without conventional electrodes, and they are connected with each other by merely inserting the projection for electromagnetic induction of the treating apparatus body into the contact lens treating vessel, the apparatus for treating contact lenses of the present invention does not suffer from the conventional problem such as insufficient contact of an electrode of the contact lens treating vessel with an electrode of the treating apparatus body, and has excellent usability.

The apparatus for treating contact lenses and the contact lens treating vessel for use therein, of the present invention are more specifically described and explained by means of the following Example. It is to be understood that the present invention is not limited to the Example.

EXAMPLE 1

As a contact lens treating vessel, a contact lens treating vessel shown in FIG. 1 was used. A bottom body 10 was equipped with an installation portion 22 for inserting a projection for electromagnetic induction 17 of a treating apparatus body 15 as shown in FIG. 2. The installation portion 22 having a concavity was formed so that the inside diameter and the depth of the installation portion 22 were 13 mm and 11 mm, respectively. An electromagnetic induction coil 12 having an outside diameter of 18 mm and the number of turns of 120 turns was formed inside the bottom body 10 so that the coil was wound on the installation portion 22. One end of the electromagnetic induction coil 12 was connected to an electrode 8a and one end of a condenser 14 having a capacity of 10 μF. through a diode which was a rectifier 13. Another end of the electromagnetic induction coil 12 was connected to another end of the condenser 14 and an electrode 8b.

The electromagnetic induction coil 12, diode 13, condenser 14, electrodes 8a and 8b were connected with leads, as shown in FIG. 1.

The electrodes 8a and 8b were fixed on a bottom panel 9. In order to insulate bottom panel 9, an ABS resin panel was used as the bottom panel 9. As the electrodes 8a and 8b, platinum electrodes having a diameter of 2.7 mm and a thickness of 0.07 mm were used, respectively.

In order to prevent the leakage of an electrolyte solution which is poured into a treating vessel body 1, a seal packing 11 made of a silicone rubber, having a U-shape in section, which is provided around the bottom panel 9, was provided between the treating vessel body 1 and the bottom body 10 to attach them tightly.

The treating vessel body 1 and the bottom body 10 were made of a transparent polycarbonate and an ABS resin, respectively. The outside diameter of each of the treating vessel body 1 and the bottom body 10 was adjusted to 25 mm, respectively.

As an electrolyte solution, 5.0 ml of an aqueous solution containing 1.3% by weight of boric acid, 0.06% by weight of borax and 0.44% by weight of sodium citrate was used, and the aqueous solution was poured into the treating vessel body 1. Soft contact lenses 3a and 3b which were commercially available from Menicon Co., Ltd., under the trade name of MENICON SOFT MA, were put in a basket 4 made of polycarbonate. Then, a gas-permeable film 6 made of a fluorocarbon resin was provided between a support 4a of the basket 4 and a lid 2. The lid 2 was put on the top of the treating vessel body 1 through the seal packing 5 made of a silicone rubber, and the lid 2 and the treating vessel body 1, which had screw threads, were engaged.

As a treating apparatus body 15, a treating apparatus body shown in FIG. 2 was used. A bezel for attachment and detachment 16 having an inside circuit diameter of 13 mm, an outside circuit diameter of 25 mm and a depth of 11 mm was provided around the projection for electromagnetic induction 17 of the treating apparatus body 15. A central projection of an E-type ferrite core 21, on which a magnetic field generating coil 18 having an outside diameter of 11 mm and the number of turns of 120 turns was wound, was inserted into the inside of the projection 17.

The magnetic field generating coil 18 was connected through a lead wire with a high frequency generating circuit 20 by which a current having a frequency of 60 Hz could be converted into a current having a frequency of 7 KHz. The high frequency generating circuit 20 was connected to a general domestic AC supply of 100 V through a plug 19.

The projection for electromagnetic induction 17 was inserted into the inside of the installation portion 22 of the contact lens treating vessel.

Then an electric current was applied to the electromagnetic induction coil 12 by electromagnetic induction. At this time, the electric current and voltage between the electrodes 8a and 8b were measured. As a result, the electric current was 100 mA and the voltage was 45 V. It took 12 minutes to raise the temperature of the electrolyte solution to 100° C.

As mentioned above, when the apparatus for treating contact lenses of the present invention is used, a treating solution which doubles as, for instance, an electrolyte solution, can be directly heated with an aid of electrical resistance of the treating solution, by directly applying electricity to the treating solution. Therefore, the temperature of the solution can be rapidly increased, and a period of time for disinfecting can be made shorter than the period of time for disinfecting by using a conventional apparatus for heating the treating solution from outside.

Any electrically connecting points of the treating apparatus body and the treating vessel are not exposed. Therefore, insufficient electrical contact is not caused by contamination of the connecting points, and the connecting points are not worn away by the repeated attachment or detachment of the treating vessel thus ensuring that that an electric current is sufficiently applied to the solution. Furthermore, since a short-circuit is unlikely when the solution is spilled during the treatment of a contact lens, the apparatus is very safe when handled.

Though one embodiment of the present invention is described above, it is to be understood that the present invention is not limited to the above-mentioned embodiment, and various changes and modification may be made in the invention without departing from the spirit and scope thereof.

What is claimed is:

1. An apparatus for treating contact lenses comprising a treating apparatus body for supplying electric power and a contact lens treating vessel which can be attached to or detached from the treating apparatus body, said treating apparatus body being equipped with a first magnetic field-generating coil and said contact lens treating vessel being equipped with a second electromagnetic induction coil, wherein said first magnetic field generating coil is constructed and arranged to fit over said second electromagnetic induction coil.

2. The apparatus of claim 1, wherein said first magnetic field-generating coil is electrically insulated from the contact lens treating vessel.

3. The apparatus of claim 1, wherein said treating apparatus body has a high-frequency oscillation circuit connected with the first magnetic field-generating coil.

4. The apparatus of claim 1, wherein said treating apparatus body has a bezel for attachment and detachment of the contact lens treating vessel and a projection containing said first magnetic field-generating coil, wherein said projection fits within said second electromagnetic induction coil when said treating apparatus body is attached to said contact lens treating vessel.

5. The apparatus of claim 1, wherein a ferrite core is provided in the first magnetic field-generating coil.

6. The apparatus of claim 1, wherein said contact lens treating vessel is equipped with an electromagnetic induction coil and a rectifier for converting alternating current into direct current; said contact lens treating vessel further including a basket, basket support and lid.

7. The contact lens treating vessel of claim 6, further including a capacitor.

8. The contact lens treating vessel of claim 7, wherein the capacity of said capacitor is 0.1 to 100 $\mu$F.

9. The contact lens treating vessel of claim 6, wherein said basket is made of polysulfone.

10. The contact lens treating vessel of claim 6, wherein said lid having air vents is provided on the top of the treating vessel body.

11. The contact lens treating vessel of claim 6, further includes a gas-permeable film through which liquid cannot pass, disposed between a support for the basket and the lid.

12. The contact lens treating vessel of claim 11, wherein said gas-permeable film has a pore diameter of 0.1 to 3.0 $\mu$m.

13. The contact lens treating vessel of claim 11, wherein said gas-permeably film is selected form the group consisting of: fluorocarbon resin film, hydrophobic microbial filter, hydrophobic microfiltration membrane made of polyethylene, hydrophobic microfiltration membrane made of polypropylene, and silicon film.

14. The contact lens treating vessel of claim 13, wherein a polypropylene net is laminated on said fluorocarbon resin film.

15. The contact lens treating vessel of claim 7, including a basket made of polycarbonate.

16. The contact lens treating vessel of claim 6, including two electrodes for applying electricity being connected with the electromagnetic induction coil to a treating solution contained therein.

* * * * *